(12) United States Patent
Vetterlein

(10) Patent No.: US 8,335,370 B2
(45) Date of Patent: Dec. 18, 2012

(54) DEVICE AND METHOD FOR EVALUATION OF A CALIBRATION ELEMENT USED IN A COLOUR PENETRATION METHOD

(75) Inventor: Thomas Vetterlein, Main (DE)

(73) Assignee: Illinois Tool Works Inc., Glenview, IL (US)

( * ) Notice: Subject to any disclaimer, the term of this patent is extended or adjusted under 35 U.S.C. 154(b) by 458 days.

(21) Appl. No.: 12/601,168

(22) PCT Filed: May 19, 2008

(86) PCT No.: PCT/US2008/064036
§ 371 (c)(1),
(2), (4) Date: Jan. 9, 2010

(87) PCT Pub. No.: WO2008/147747
PCT Pub. Date: Dec. 4, 2008

(65) Prior Publication Data
US 2010/0158350 A1   Jun. 24, 2010

(30) Foreign Application Priority Data
May 22, 2007 (DE) .................. 10 2007 024 059

(51) Int. Cl.
*G06K 9/00* (2006.01)
*G06K 7/00* (2006.01)
*G06K 9/20* (2006.01)
(52) U.S. Cl. .................. 382/152; 382/141; 382/312
(58) Field of Classification Search ........... 382/141–152
See application file for complete search history.

(56) References Cited

U.S. PATENT DOCUMENTS

| | | | | |
|---|---|---|---|---|
| 4,621,193 A * | 11/1986 | Van Hoye | | 250/302 |
| 4,845,356 A * | 7/1989 | Baker | | 250/225 |
| 5,003,831 A | 4/1991 | Link et al. | | |
| 5,652,428 A * | 7/1997 | Nishioka et al. | | 850/4 |
| 6,476,385 B1 * | 11/2002 | Albert | | 250/302 |
| 2007/0097360 A1 * | 5/2007 | Beaume | | 356/237.1 |

FOREIGN PATENT DOCUMENTS
DE    3144379 A1    5/1983
(Continued)

OTHER PUBLICATIONS

Filinov et al "Penetrant Testing: The Software Tool for Comparison of Sensitivity and Estimation of Contrasts, Color and Brightness Characteristics of Penetrant Systems" ECNDT 2006, Th.1.8.4, pp. 1-10.*

(Continued)

*Primary Examiner* — Gregory J Toatley
*Assistant Examiner* — Jarreas C Underwood
(74) *Attorney, Agent, or Firm* — Lowe Hauptman Ham & Berner LLP

(57) ABSTRACT

The invention relates to an apparatus rating a monitoring element to which is or was applied a dye penetrant procedure and which is fitted with at least one artificial defect in the form of at least one indentation, the apparatus including an image recorder generating an image of at least parts of the monitoring element, said parts comprising at least portions of the minimum of one artificial defect, said apparatus including an image analyzer rating the image generated by the image recorder, and to a corresponding method.

16 Claims, 2 Drawing Sheets

FOREIGN PATENT DOCUMENTS

Figure 1:
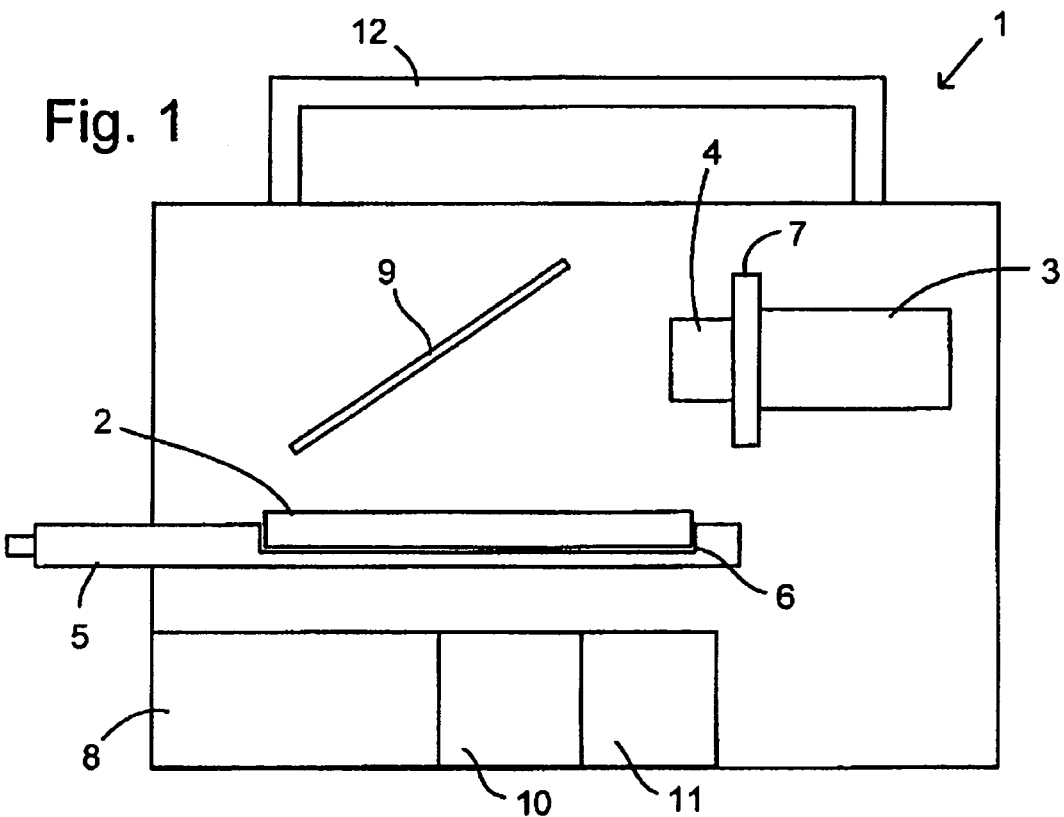

| | | |
|---|---|---|
| DE | 3602395 A1 | 7/1987 |
| DE | 8608690 U1 | 8/1987 |
| DE | 270143 A1 | 7/1989 |
| DE | 3907732 A1 | 9/1990 |
| DE | 19645377 A1 | 5/1998 |
| DE | 19902525 A1 | 8/2000 |
| EP | 0045899 A1 | 2/1982 |

OTHER PUBLICATIONS

Sam J. Robinson et al., "ASTM E-1417 Penetrant System Check: New Requirements and Test Pieces," The American Society for Nondestructive Testing, XP-002493543.

Mikhail V. Filinov et al., "Penetrant Testing: The Software Tool for Comparison of Senstivity and Estimation of Contrasts, Color and Brightness Characteristics of Penetrant Systems," ECNDT 2006—Th. 1.8.4, pp. 1-10, XP-002493542.

Sam J. Robinson et al., "ASTM E-1417 Penetrant System Check: New Requirements and Test Pieces," The American Society for Nondestructive Testing, XP-002493543, Copyright 2008.

DE Search Report for 10 2007 024 059.9 dated Jan. 17, 2008.

ISR and WO for PCT/US2008/064036 dated Sep. 8, 2008.

\* cited by examiner

DEVICE AND METHOD FOR EVALUATION OF A CALIBRATION ELEMENT USED IN A COLOUR PENETRATION METHOD

RELATED APPLICATIONS

The present application is national phase of PCT/US2008/064036 filed May 19, 2008, and claims priority from German Application Number 10 2007 024 059.9 filed May 22, 2007, the disclosures of which are hereby incorporated by reference herein in their entirety.

The present invention relates to a device, hereafter apparatus, for evaluating, hereafter rating, a calibration element, hereafter monitoring element, which may be or was subjected to a colour penetration method, hereafter dye penetrant procedure, also to a method for calibrating, hereafter rating such a monitoring element as respectively defined in the preambles of claims 1 and 2.

Increasingly novel and in particular non-magnetic materials have been used in recent times in both the automotive and aircraft industries, the dye penetrant procedure assumes increasing significance in non-destructive testing. The reason is that non-magnetic materials such as aluminum or also ceramic and carbon-fiber composite materials cannot be tested using the widespread magnetic particle inspections.

In a first stage of the dye penetrant procedure, a migrating penetrant which fluoresces when irradiated with uv is deposited on the surface of the workpiece to be tested. In general the penetrant deposition is in the form of spraying the workpiece with a penetrant, also dipping it into a bath of penetrant.

After the penetrant has been deposited, it is allowed for a given dwell time to migrate into defects in the material, said defects being open toward the surface, this process being caused by adhesion and capillary effects. After said predetermined dwell time, the workpiece is washed in a manner precisely defined by such boundary conditions as duration, water pressure and water temperature to avert excessively washing the penetrant.

After the cleansed surfaced has been dried applying hot air, the stage of "bleeding" begins. During this stage the penetrant that had been situated in the defects open at the surface (for instance pores or cracks) will migrate back to and on the workpiece's surface. This procedure is frequently optimized/enhanced by depositing a developer at said worpkpiece's surface. Illustratively said developer may be a fine-grain powder or a solution which when dried leaves behind powdery residues. In this process the penetrant diffuses into the developer. Following a predetermined and accurately defined time interval, the surface flaws and defects are detected using an uv lamp.

To assure that the dye penetrant process parameters were selected optimally and the workpiece defects were reliably detected, a monitoring element—which is fitted itself with artificial defects such as star-shaped defects or other, similarly deposited surface damages to be detected—is subjected at regular intervals to the same process as are the workpieces to be tested. This monitoring element then is sanctioned by a technician or checking operator who simultaneously also may be charged with carrying out workpiece quality control using uv light. If the artificial defects are clearly visible, this fact is manually logged by the checking operator into a book. If said defects are not sufficiently visible, the process parameters of dye penetrant treatment must be adjusted accordingly. This fact also is manually logged by the checking operator.

Besides a "human factor" being introduced when rating the monitoring element, that is, different checking operators may rate the observed intensities differently, logging-in manually also demands considerable time and hence expense. Frequently too the tested workpiece's buyer requires test documentation, so that the expense is higher still due to the paper work.

Accordingly it is the objective of the present invention to create apparatus rating a monitoring element to which a dye penetrant procedure was applied or is yet applicable, said apparatus allowing objectively rating the monitoring element and reducing checking operator labor. A further objective of the present invention is to create a method for rating such a monitoring element, said method also reliably rating in objective manner this monitoring element, simultaneously thereby the workload of the pertinent checking operator being reduced and the rating being attained independently of a checking operator.

These objectives of the present invention are attained by means of apparatus rating a monitoring element to be or already subjected to a dye penetrant procedure as defined by claim 1. The procedural part of said objectives is attained by a method rating a monitoring element of a dye penetrant procedure defined in claim 12.

Further features of the present invention are defined in the dependent claims. The invention is elucidated in illustrative manner below in relation to the appended drawings.

Figure 2:
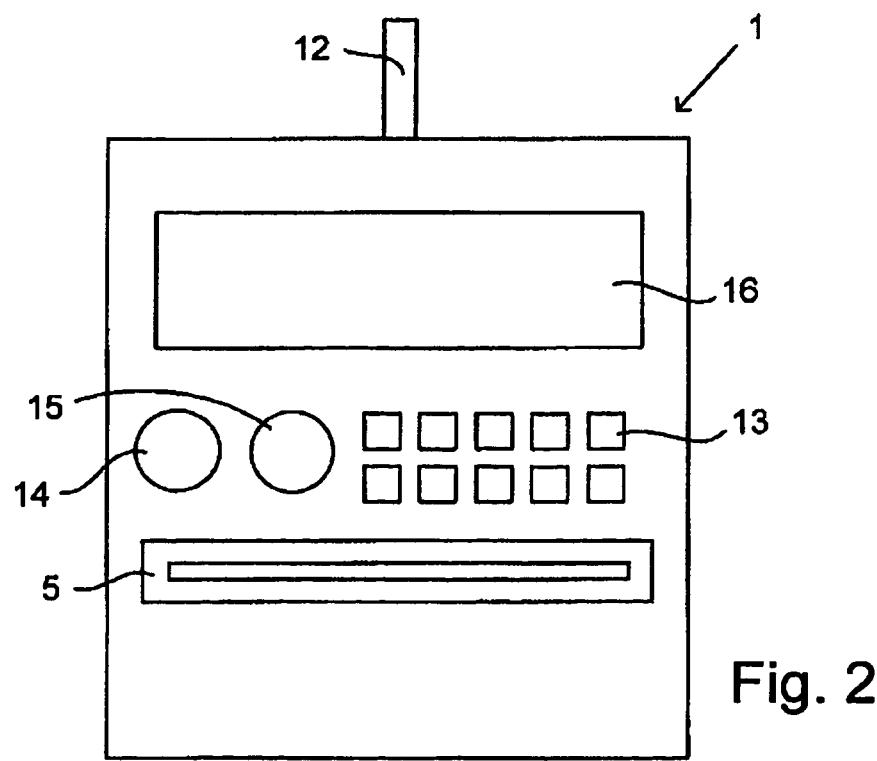
Figure 3:
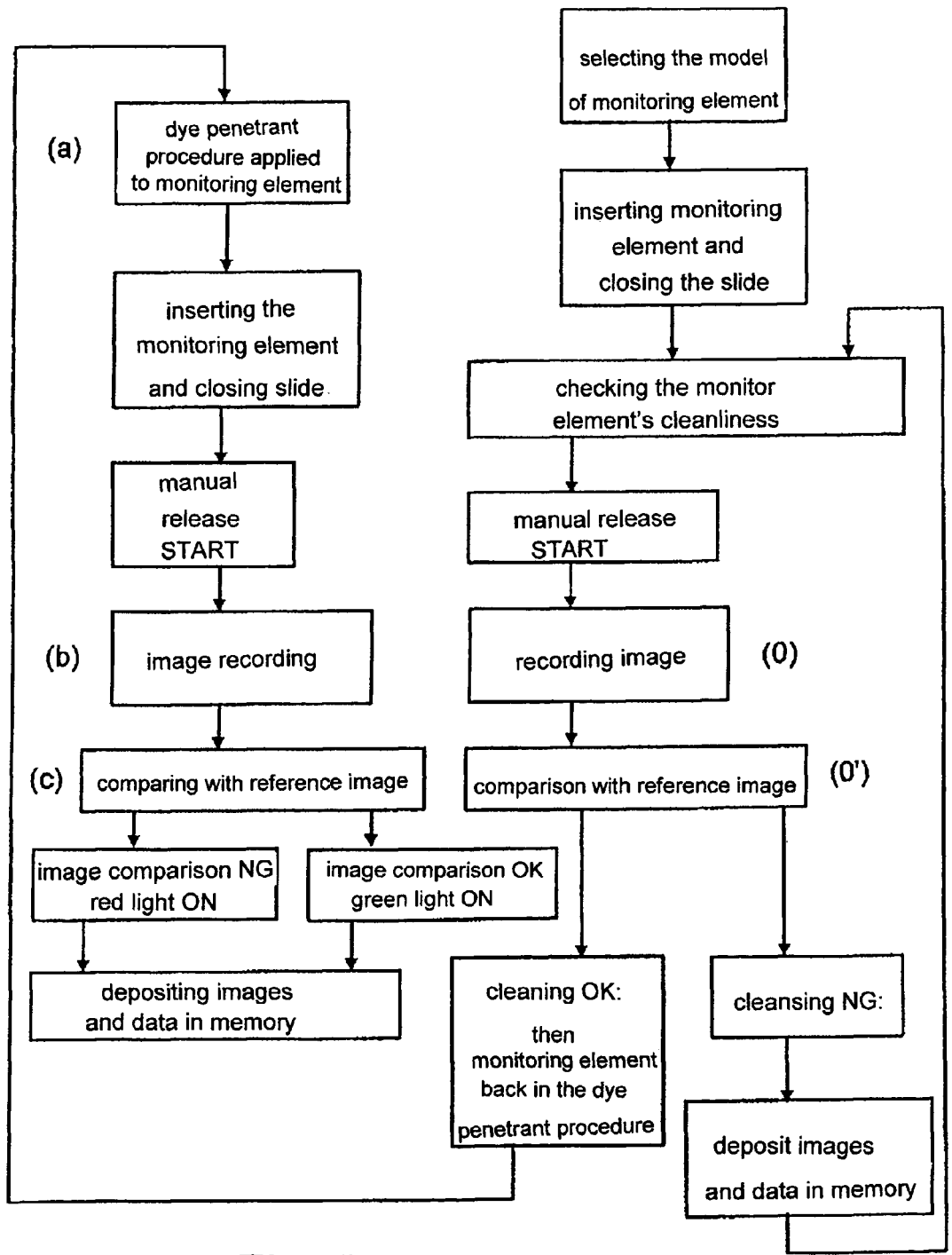

FIG. 1 is a schematic, cross-sectional view of a preferred embodiment of apparatus of the invention, FIG. 2 schematically shows the preferred embodiment of FIG. 1 in topview and FIG. 3 is a flow chart of a preferred mode of implementation of a method of the invention.

As shown in FIG. 1, the apparatus 1 rates a test element 2 to which a dye penetrant procedure my be applied or already was and which is fitted with at least one artificial defect open toward the surface of the monitoring element 2 in the form of an indentation, further comprises an image recorder in the form of a CCD camera 3 fitted with an objective lens 4. The CCD camera 3 and lens 4 together generate an image of at least parts of the monitoring element 2, said parts at least comprising one artificial defect. In the preferred embodiment mode of the present invention, the monitoring element 2 comprises five star-shaped indentations with different line widths, all said five stellate defects being detected by the CCD camera 3 which is fitted with a USB interface.

To generate the image of the monitoring element 2, same is positioned on an insertion slide 5 which may be pulled out of the apparatus 1 as if it were a drawer to allow receiving the monitoring element 2 and then is reinserted. A recess 6 in said slide 5 receives the monitoring element 2 and assures it remains firmly in position on the slide 5. The dimensions of the recess are such that the monitoring element 2 can be placed in it and be simultaneously held firmly in position. To record an image of the monitoring element 2, it is illuminated by an illuminator 7 which in the preferred embodiment mode consists of circularly arrayed uv LEDs. Obviously other light sources may be used alternatively, for instance circularly arrayed mercury or xenon vapor lamps. A circular array is not mandatory either, however this configuration of the illuminator 7 around the zone of the lens 4 of the CCD camera 3 eliminates stop interferences (backlighting, scattered light etc.) when generating the images.

To rate the condition of the monitoring element 2, the apparatus 1 is fitted with an image analyzer rating the image generated by the CCD camera 3. In the preferred embodiment mode of the apparatus 1 of the present invention, the image analyzer includes an image comparator 8 comparing the image generated by the image recorder 3 with a reference image. In addition to or alternatively to the image comparator 8, the image analyzer may comprise line sequence means rating the image generated by image recorder using a line sequence algorithm for detecting or filtering out lines, i.e., edges or serires of adjacent pixels, that have a predetermined contrast to the background. Further components of the image analyzer based for instance on a classifying algorithm or other image rating procedures also are conceivable and applicable.

Instead of the CCD camera, which may be black and white or color, other cameras are applicable also, for instance an interlaced camera, progressive scan camera, CMOS camera (which is able to process high contrasts), or a digital camera. Instead of a USB interface, the camera and also the image analyzer may be fitted with an IEEE or a RS232 or a serial or parallel interface, or a network or a wireless interface. The CCD camera 3 may be integrated for instance using a grabber element (grabber card) or a fire-wire interface.

In order to assure utmost compactness, said apparatus of the invention moreover is fitted with a deflecting mirror 9 deflecting the image of the horizontal monitoring element into the objective 4 (also horizontal) of the CCD camera 3. This configuration offers compact positioning of the control element 2 and the CCD camera 3.

The image comparator 8 includes a reference image memory 10 allowing storing at least one reference image serving as the reference image for the image comparator 8. Moreover the apparatus 1 includes a logging unit 11 to log the images generated by the image recorder 3 and the ratings from the image analyzer, as a result of which a log of the operation of the apparatus 1 may be retrieved any time.

It should be borne in mind in this respect that the apparatus 1 was designed to automatically rate the monitoring element 2 and in its in its described preferred embodiment mode also being portable (carrying grip 12), allowing carrying said apparatus from one test station where a dye penetrant procedure is applied to the next test station where such a method shall be applied.

A rating method of the present invention to rate a monitoring element 2 for a dye penetrant procedure takes place as follows (also see the flow chart of FIG. 3).

The dye penetrant procedure is carried out in a first stage (a) at the monitoring element 2. In other words, the monitoring element 2 together with workpieces to be tested is subjected to the dye penetrant procedure. Following this dye penetrant procedure and a selection of the type of monitoring element by means key board 13 configured at the front side of the apparatus 1, and upon insertion of the monitoring element 2 in the receiving slide 5—and after a manual release using the keyboard 13—then, in a stage (b), the CCD camera 3 generates an image of at least part of the monitoring element 2 displaying at least a portion of an artificial defect. In the present embodiment mode, the entire zone comprising the five star-shaped indentations are recorded by the CCD camera 3. In a further stage (c), the image generated by the CCD camera 3 is rated by an image analyzer of which the output indicates the condition of the monitoring element.

In the preferred mode of implementation of the method of the invention, the stage (c) includes comparing, by means of the image comparator 8, an image generated by the CCD camera 3 with a reference image. In the preferred mode of implementation the reference image is an image of the same portion of a monitoring element of the same model, of which the condition must be rated, and which offers an optimal defect detection. In other words, the comparison is with an image of which the artificial defects are optimally displayed by the previously applied dye penetrant procedure. This shall be the case in the preferred mode of implementation when the five stars configured at the monitoring element are optimally visible under uv light.

Be it borne in mind in this respect that besides image comparison also arbitrary other image analyses may be used, in particular procedures based on a line sequence algorithm respectively a classification algorithm.

When the image analyzer output indicates that the condition of the monitoring element 2 is adequate to continue applying the dye penetrant procedure to the workpieces with the same parameters, then a light 14 (which is green in the preferred embodiment mode) lights up at the front side (FIG. 2) indicating the procedure is OK. If however the output is unsatisfactory, a red light 15 lights up (NG) indicating that the dye penetrant procedure parameters must be changed/altered.

As regards the preferred mode of implementation of the method of the invention, an image is generated not only following the dye penetrant procedure applied to the monitoring element 2, but also prior to it (stage [0]). The same portion of the monitoring element 2 is involved that shall be illuminated subsequently to the application of the dye penetrant procedure. For that purpose the cleansed monitoring element 2 is again inserted by the insertion slide into the apparatus 1 and, following manual release, using the keyboard 13, shall be photographed by the CCD camera 3.

After an image of the control element 2 has been generated by the CCD camera 3, said image is rated (step [0']) by the image analyzer, in the form of the image comparator 8, to ascertain in this manner the degree of cleanliness of this monitoring element 2. This procedure assures the absence of any previous penetrant residues at the monitoring element 2 before it shall be subjected to the dye penetrant procedure. If said degree of cleanliness is within a predetermined range of quality, then this condition is displayed by the green lamp 14, namely the dye penetrant procedure may be now be applied, whereas in the other case the red light indicates that the monitoring element 2 must be cleansed. Once cleansed, said monitoring element must again be subjected to the stages (0) and (0').

In the preferred mode of implementation, the stage of image analysis prior to the dye penetrant procedure also includes comparing the image generated by the image recorder, respectively the CCD camera 3, with the reference image, using the image comparator 8. In this procedure too the comparison takes place with that reference image which is fitted with optimally configured five stars. When checking the degree of cleanliness of the monitoring element 2, the decision criterion is the magnitude of the difference between the two images, whereas the decision on the condition of the monitoring element 2 after it was subjected to the dye penetrant procedure is determined by the largest possible congruence. Alternatively, the reference image also might be that of a clean monitoring element 2, or even of two reference images (for instance one of a clean monitoring element 2 and one with the best possible display). A still larger number of reference images may even be considered, in which event the comparison might apply to finding the state of the monitoring element closest to one of the reference images. In the preferred mode of implementation of the method of the invention, the reference image(s) is/are recorded/stored in the image comparator.

Instructions to the checking operator as well as the rating results (also indicated by lamps 14, 15) are shown (additionally) in clear text on a display 16 (FIG. 2).

Ultimately All images and all checks and ratings are deposited/stored in the log 11. In the preferred embodiment mode of the invention, this log is a memory that can be linked to a computer network. Also this memory can be connected to a portable or fixed printer allowing log printout and if need be electronic forwarding.

Even though the invention was discussed above in relation to embodiment and implementation modes of fixed feature combinations, it includes also further conceivable and advantageous combinations defined in particular but not in limiting manner in the dependent claims. All features disclosed in the application documents are claimed as being inventive to the extent that, whether in combination or alone, they are novel with respect to the state of the art.

The invention claimed is:

1. An apparatus for rating a degree of cleanliness of a monitoring element to which a dye penetrant procedure is to be applied and which has at least one artificial defect in the form of an indentation, the apparatus comprising:
   an image recorder configured to generate an image of at least a part of the monitoring element including at least a portion of the at least one artificial defect;
   an image analyzer configured to rate the degree of cleanliness of the monitoring element based on the image generated by the image recorder, the image analyzer including an image comparator configured to compare the image generated by the image recorder and a reference image; and
   a display unit configured to display a result of rating by the image analyzer, the result of rating indicating whether to proceed to a next stage procedure, wherein
   the image comparator is configured to compare magnitudes of the image generated by the image recorder and the reference image.

2. The apparatus as claimed in claim 1, wherein the image analyzer further includes a line sequence unit configured to rate the image generated by the image recorder using a line sequence algorithm.

3. The apparatus as claimed in claim 1, wherein the image recorder is a USB compatible CCD camera.

4. The apparatus as claimed in claim 1, further comprising an illuminator configured to illuminate the monitoring element when the image recorder generates the image.

5. The apparatus as claimed in claim 4, wherein the illuminator is an annular UV lamp or annularly arranged UV LEDs.

6. The apparatus as claimed in claim 1, further comprising a deflecting mirror for deflecting light reflected at the monitoring element to the image recorder.

7. The apparatus as claimed in claim 1, wherein the image analyzer further includes a reference image memory for storing the reference image.

8. The apparatus as claimed in claim 1, further comprising a log unit for logging at least one of the image generated by the image recorder, data generated by the image analyzer, or the result of rating by the image analyzer.

9. The apparatus as claimed in claim 8, wherein the log unit is configured to log the at least one of the image generated by the image recorder, the data generated by the image analyzer, or the result of rating by the image analyzer in an automatic manner.

10. The apparatus as claimed in claim 1, wherein the apparatus is portable.

11. A method of rating a degree of cleanliness of a monitoring element in a dye penetrant procedure, the monitoring element having at least one artificial defect in the form of at least one indentation, the method comprising:
    generating, using an image recorder, an image of at least a part of the monitoring element including a portion of the at least one artificial defect;
    rating, using an image analyzer, the degree of cleanliness of the monitoring element based on the image generated by the image recorder, the rating including comparing, using an image comparator, the generated image and a reference image; and
    displaying a result of rating on a display unit, the result of rating indicating whether to proceed to a next stage procedure, wherein
    the comparing includes comparing magnitudes of the generated image and the reference image.

12. The method as claimed in claim 11, further comprising storing the reference image in a reference image memory.

13. The method as claimed in claim 11, further comprising logging at least one of the image generated by the image recorder, data generated by the image analyzer, or the result of rating.

14. The method as claimed in claim 11, further comprising illuminating the monitoring element when the image recorder generates the image.

15. The method as claimed in claim 14, wherein the illuminating includes illuminating the monitoring element with an annular UV lamp or annularly arranged UV LEDs.

16. The method as claimed in claim 11, further comprising deflecting light reflected at the monitoring element to the image recorder.

* * * * *